US00PP09638P

United States Patent [19]

Watson et al.

[11] Patent Number: Plant 9,638

[45] Date of Patent: Sep. 3, 1996

[54] PLUM CULTIVAR 'CASTLETON'

[75] Inventors: John P. Watson, deceased, late of Phelps, by Judith Watson, executor; Robert L. Andersen; Kenneth G. Livermore, both of Geneva,, all of N.Y.

[73] Assignee: Cornell Research Foundation, Inc., Ithaca, N.Y.

[21] Appl. No.: 148,085

[22] Filed: Nov. 4, 1993

[51] Int. Cl.[6] ..... A01H 5/00

[52] U.S. Cl. ..... Plt./38.1

[58] Field of Search ..... Plt./38.1, 38.2

*Primary Examiner*—James R. Feyrer

*Attorney, Agent, or Firm*—Jones, Tullar & Cooper

[57] ABSTRACT

A new distinctive cultivar of plum (*Prunus domestica*) named 'Castleton' (formerly tested as NY 66.609.4) which is exceptional in combining (1) high quality, attractive dark purple fruit capable of achieving in mid-August sufficient color for commercial fresh markets, (2), a tree habit that has fewer lateral and secondary lateral branches than other competing commercial cultivars and which facilitates ease of harvesting, and (3) fruit quality and pit conformation traits coupled with consistent, high yield potential which favor it for commercial processing uses.

2 Drawing Sheets

BACKGROUND OF THE INVENTION

In 1966 ninety-one hybrid plum seeds were created from controlled pollinations between 'Valor' × 'Iroquois'. A population of seedlings with the New York State Agricultural Experiment Station breeding record designation NY 66.609 were planted in 1967 in an orchard designated as Crittenden 30 in Row 7 Trees #124 through #215. One seedling in this population was planted at Cr30R7T#165. In 1972 it fruited for the first time and in 1974 it was selected for further testing because of its early ripening season and its high quality and interesting dark purple colored fruit. It was designated NY 66.609.4 and grafted in 1974 at the New York State Agricultural Experiment Station, Geneva, N.Y. 14456 to Myrobolan,' a seedling plum rootstock, utilizing the nursery t-budding grafting technique. These grafts produced trees to be used for more tests of this selection's merit. Grafted trees that resulted were planted in 1976 in a Station field designated as Crittenden 22R10T1, T2 and Cr22R13T19, T20, T21. In 1983 further grafted trees resulted from using buds taken from Cr30R7T165 for propagating wood and subsequently these grafted nursery trees were planted at Cr23 R5T27. T28, T29. In the ensuing years third clonal generation trees were created utilizing buds for propagating wood taken from the Cr22R10 and Cr22R13 trees. Such third generation trees were distributed under redistricted, nondistribution test agreements to collaborators in the USA and Canada who assisted us in evaluating the merit of this selection.

NY 66.609.4 is being named and released as 'Castleton' and is the subject of this invention.

DESCRIPTION OF RELATED ART

In all test plantings, trees of NY 66.609.4 (named and released as 'Castleton' on Nov. 4, 1993) bore consistently good fruit crops as judged by experienced researchers and plum orchardists. Some of these trees were tested during blossom time for pollenizer effectiveness to determine if the selection had the self fruitful characteristic, such tests proved it to be partially self fruitful.

There follows comparison of traits of this selection as compared to the 'Stanley' cultivar that is the primary commercial European-type plum cultivar in the Great Lakes Region, comprising over 75% of all plum orchards there.

DESCRIPTION OF THE INVENTION

This invention relates to a new and distinctive cultivar of the European-type plum tree. This type of plum is also known in the commercial fruit trade in the USA as a prune-plum since all dried prunes in the USA maket are derived from *Prunus domestica,* as is 'Castleton'. We discovered 'Castleton' in a test planting belonging to the New York State Agricultural Experiment Station, Cornell University, Geneva, Ontario County, N.Y. This discovery is a product of a plum breeding research program of the New York State Agricultural Experiment Station.

POLLINATION

We have conducted experiments to determine the pollination biology specifics about 'Castleton'. In Geneva it flowers open about one day earlier than 'Stanley's'. Our experiments took the form of numerous field tests to cover the emerging flowers with paper bags and thereby isolate flowers of 'Castleton' from bee visitation. Such bagging allowed us to conduct two kinds of pollination tests: (1) effects of wind and gravity in moving 'Castleton's' own pollen to the stigmas of 'Castleton' flowers within such bags, and (2) effects of emasculating the male portions of bagged flowers prior to their shedding pollen and then applying foreign pollen from known sources to determine which cultivars produce pollen that is effective in pollinating 'Castleton'. In all cases some fruit with mature seeds were produced without cross pollination but slightly fewer such fruit were obtained from 'Castleton' than from similarly tested 'Stanley'. 'Stanley' pollen was highly effective in pollenizing 'Castleton'. Hence, we conclude that 'Castleton' is partially self fruitful and could be planted as individual trees which will not require a pollenizer cultivar, but they would benefit in some seasons from pollenizing by 'Stanley' or another pollen compatible cultivar.

DETAILED PLANT DESCRIPTION

Accompanying FIGS. 1 thru 5 depict leaves, fruits, and pits as well as the entact tree. The numerical color specifications employed in this patent disclosure are those of the Royal Horticultural Society Colour Chart (1976):

FLOWERS AND FLOWERING

Flowers born on lateral branches or spurs on branches that are two years old or older. They also are born for axillary buds of shoots laid down the previous growing season. Typically, 3 to 5 flowers are produced from spur buds and 3 to 5 fowers are also borne on axiallary buds on the previous season's shoots. Such flowers emerge in Geneva about one day earlier than they do on the 'Stanley' cultivar.

Flowers are white, single and have no unusual features that distinguish them from those of other plum cultivars except that their pedicels are shorter than many others. They are structurally typical of 'Prunus domesticawith a base number of five petals and about 35 stamens. Pedicels are quite short often only 2 l cm, whereas 'Stanley's' are usually over 3 cm in length.

FRUITING HABIT AND FRUIT

Figure 5:
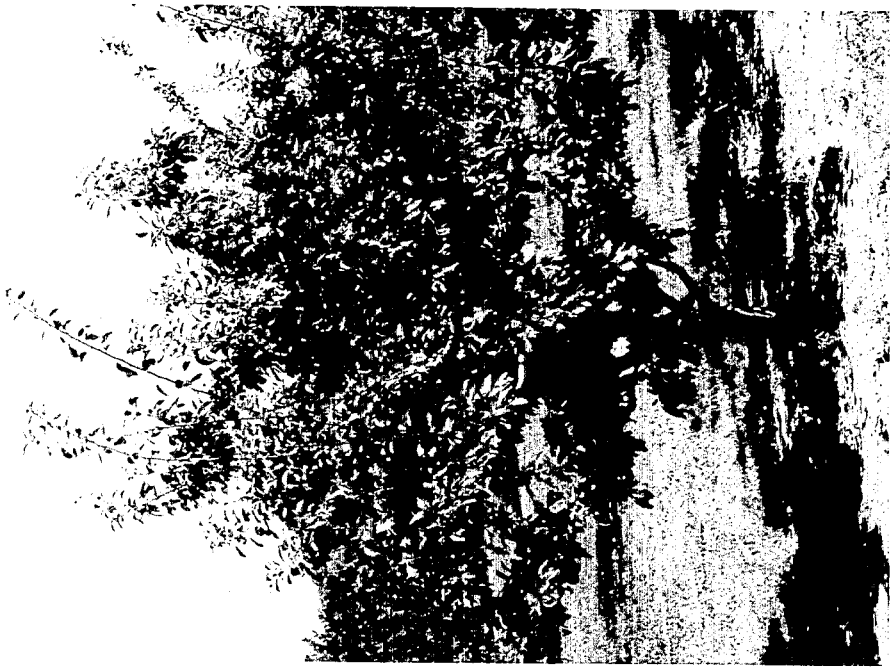
FIG. 5. 'Castleton' tree

'Castleton' trees FIG. 5 which are grafted to the common plum rootstock, 'Myrobolan Seedling', typically have flowers produced after three growing seasons on trees that have been planted in their orchard position. Fruit is often set on trees which flower for the first time.

Figure 1:
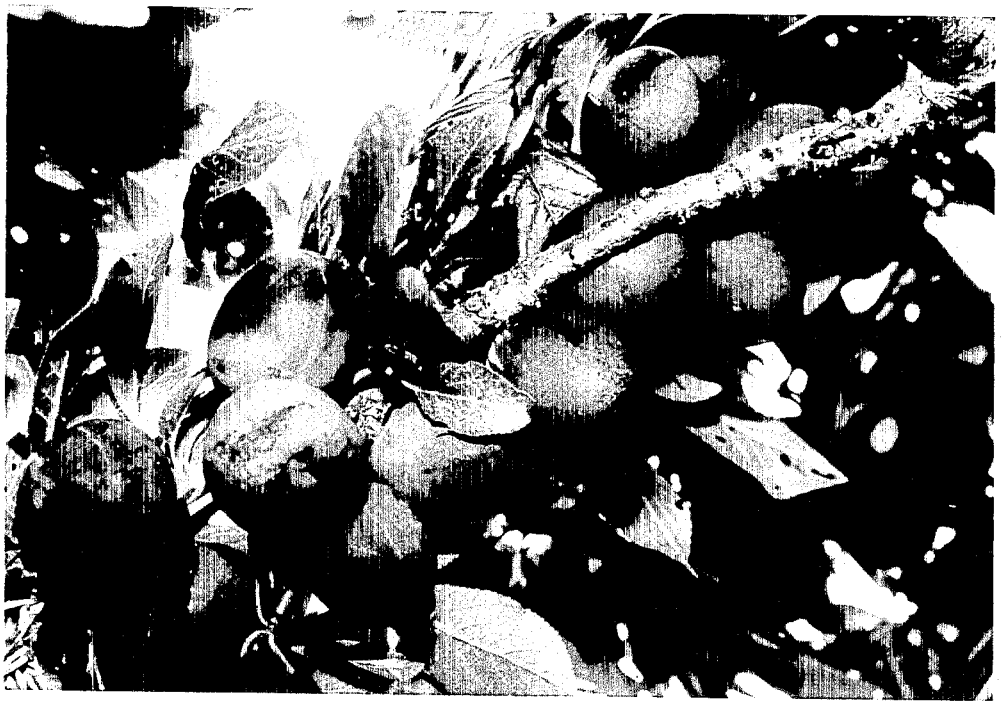
FIG. 1. Growing fruit of 'Castleton'
Figure 2:
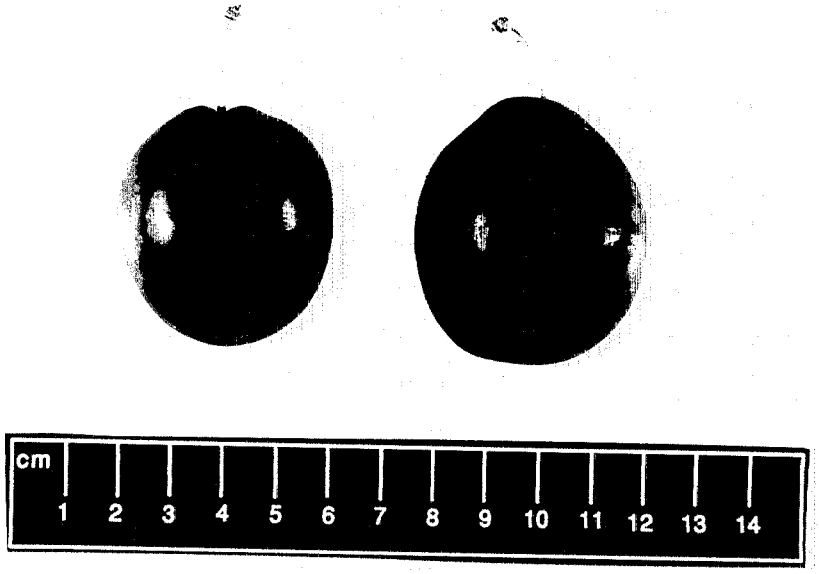
FIG. 2. Fruit of 'Castleton'
Figure 3:
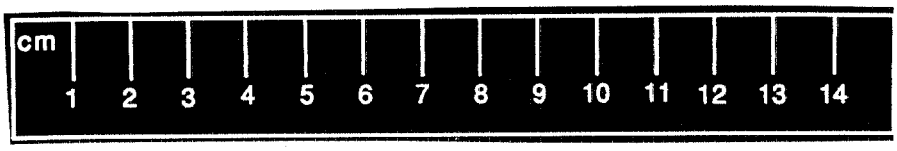
FIG. 3. Pit of 'Castleton'

The individual fruits of 'Castleton' FIGS. 1 and 2 are oblong/conic and are very symmetrical, and medium size compared to most other European-type plum cultivars. They are about 3.6 cm in cheek to cheek diameter, about 3.8 cm in suture diameter and 4.6 cm in length. They are less pointed on both the stem and stigmatic ends than 'Stanley' fruits. Their skin color at maturity is greyed-purple 87A with very little surface wax present to mask this appearance, whereas the 'Stanley' skin color is blue group 103A in mottled portions without surface wax, but surface wax often covers most of the skin and gives violet-blue group 98D color in areas where the surface wax is undisturbed. 'Castleton's' flesh color is yellow-green 153D at full tree-ripe, similar to 'Stanley', but then turns to yellow-green 152C as it approaches over-ripe status. Pits FIG. 3 are usually completely free from the flesh at hard-ripe picking stage. Their shape is oblong with more bluntness on the stigmatic end than on the stem end giving the an almond-like appearance, whereas 'Stanley's' pit often partially clings to the flesh and is more symmetrical, thinner and distinctly more pointed on both ends. The pit dimensions of 'Castleton' are 2.5×1.7×0.9 cm, whereas 'Stanley's' similar measurements are 3.0×1.4× 0.8 cm. A typical fruit is shown in FIG. 2. Fruits of 'Castleton' resist fruit cracking along the suture which is a common negative phenomenon with 'Stanley.' The flavor of 'Castleton' fruits is excellent, being pleasantly sweet and possessing good plum aroma/taste with minimal astringency. The good balance of natural sugars and natural acidity makes the quality of its fruit praticularly appealing. The fruit texture is smooth, with little grainy, stringy mouthfeel. Their flesh is firmer than many other plum cultivars and fruit retain firmness well, both on the tree and in cold storage subsequent to harvest. Fruit ripening is about 105 to 110 days after full bloom in Geneva, about 20 l to 25 days earlier than 'Stanley'.

TREE HABIT

'Castleton's' tree FIG. 5 is medium in vigor, spreading in form with an intermediate level of lateral branching. Scaffold branches are less prone to produce secondary lateral branches than 'Stanley' and this characteristic produces a tree that is heavily spurred and slightly more open to the sun's penetration to the interior of the tree than trees of 'Stanley'. This tree habit and branching structure leads to a natural oblong/conic form to the upper half of the tree crown and a rounder shape of the lower half of the mature trees.

SHOOTS

'Castleton's' shoots are of medium length with many fruiting spurs formed on two year old lateral vegetative bud positions. They have many tiny, round lenticels on the bark on the proximal ends. In the autumn after cessation of terminal growth, the color of the bark at the fourth internode above the proximal position is greyed-orange 175A, whereas 'Stanley's' is greyed-orange 166A.

LEAVES

Figure 4:
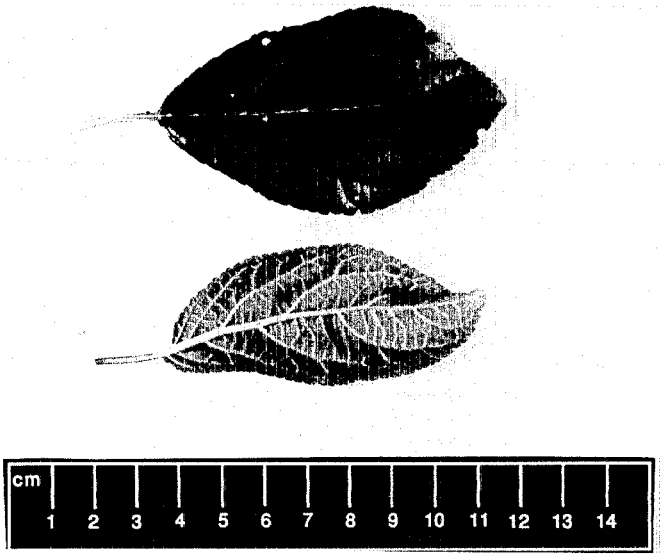
FIG. 4. Leaf of 'Castleton'

Leaves of 'Castleton' FIG. 4 are medium in leaf area, usually symmetrical, lamella glabrous and smooth with adaxial lamella surface yellow-green 137A, abaxial surface yellow-green 148C. Whereas, by contrast 'Stanley's' similar leaf surfaces are yellow-green 137B and 138B. Margins rounds serrate with 4 to 4.5 serrations per cm and serrations are shallow in their indent, usually about one mm. Whereas, by contrast 'Stanley's' serrations are usually deeper and number 3.5 per cm.

For nursery whips growing for their first season after grafting, the average number of leaves in the first 30 cm distal to the trunk on lateral shoots of over 60 cm length on 'Myrobolan Seedling' rootstocks is 14. Similarly when 'Castleton' scions are grafted to 'GF 655-2' rootstocks they average 21 leaves. 'Castleton's' leaf color on the adaxial lamella surface is yellow-green 137A, abaxial surface is yellow-green 148C, whereas the same surfaces for 'Stanley' are 137B and 138B. On average, there are 2 small, round, glands on 'Castleton' leaves which are positioned opposite to each other; and usually the larger of the 2 glands is located on the petiole, itself, as opposed to the leaf blade edge. Occasionally a third rudimentary gland is stacked beside the larger gland on the next serration tip. Variation between positions and number are high both within plants and between plants but gland shape is constantly round.

BARK

At Geneva, N.Y. the color of the bark on the north side of the trunks of mature, fruiting trees at 50 cm above the soil lines is gray group 201B with patches of mottled grayed orange 176B, whereas, 'Stanley' at a similar position is darker, gray group 201A with patches of grayed orange 177C interspersed. Lenticulas of 'Castleton' are wart-like protrusions (raised rough edged masses of tissues) when located on older wood of the trunk and larger scaffolds. They appear in discontinuous strings encircling the trunk and these strings are often 2 to 3 cm wide. 'Stanley' by contrast at similar positions has smoother, much smaller (usually less than one cm wide) lenticulas which are less numerous. The 'Italian Prune' cultivar's lenticulas are in continuous strings that encircle the entire trunk and have smoother surface than either 'Castleton's' or 'Stanley's'. The texture of the park in this portion of the tree is smooth and usually the trunk's bark doesn't begin to fragment into segmented areas until mature trees are over 10 years old, and then only on the low portions of the trunk near the ground line.

PESTS

At Geneva, trees of 'Castleton' have been kept free of common pollen born viruses of prunes, as proven by frequent indexing of the trees utilizing common herbaceous indicators like cucumber and *Chenopodium quinoa.* Susceptibility to such viruses is therefore, unknown. Other important viruses diseases of plum have not been evaluated, nor has the unique scion/rootstock susceptibility to Tomato ringspot virus strains that so devastate 'Stanley' when it is grafted to 'Myrobolan Seedling' and planted in soils infected with nematode vectors of this common virus. Experiments are underway to ascertain if 'Castleton' is different in reaction to this important disease than 'Stanley', but results are several years from being interpretable. Other serious fungal and bacterial disease of plums that have been observed in orchard trails with 'Castleton' are brown rot, black know and leaf spot. 'Castleton' is slightly more susceptible to brown rot that is 'Stanley' but similar to 'Veeblue' and several strains of early 'Italian Prune' in level of infections. Black know susceptibility of 'Castleton' wood has not been well tested due to lack of a satisfactory pathological protocol for such tests. No symptoms of leaf spot have ever been noted on the leaves of 'Castleton' even when neighboring trees of many *Prunus domestica* cultivars have been severe levels of infection and defoliation. Tolerance to fungal cankers that affect the wood of various Prunus species is above average compared to all other cultivars and genetically distinct seedlings that the inventors have evaluated for this disorder. Tolerance to European red mites is better in the 'Castleton' cultivar than for 'Stanley' as determined by orchard counts on leaves of neighboring trees and by observation of degree of "bronzing" of such trees due to mite feeding.

TRAINING AND PRUNING REQUIREMENTS

Of the 'Castleton' tree are similar to that used for 'Stanley' when grown for commercial shake-and-catch harvest for processing of its fruit or for fresh marketing. 'Castleton' is well adapted to the modified central leader system of training and pruning because it has moderate levels of apical dominance of its branches and medium vigor with an natural tendency to spread and make sufficient but not excessive numbers of lateral and secondary lateral branches. Medium tree density per acre is expected to be employed with the central modified central leader training system so that orchard implements like trunk shakers can be moved between rows and fitted between trees in the rows. Annual pruning is needed for mature modified central leader system trees to remain productive from young spurs that are re-established by invigorating trees by dormant season heading and limb removal cuts. During the early years of training of modified central leader trees some summer pruning to remove excessive growth in unwanted, excessive water shoot growth in the central portion of the crown of the tree will be required.

If 'Castleton' were to be planted in high density orchard systems rootstock research would have to first be accomplished to determine which stocks impart sufficient size control to fit the spacing that is dictated by both the soil type, soil fertility, water availability, and specific management plans for the orchard system. 'Castleton' has not yet been the subject of such intense, specific research that might be accomplished so as to optimize its performance in any one of many potential high density orchard systems in a diverse array of orchard soil environments.

Scaffold limb strength has not been objectively measured but the inventors' experience in observing abundant crops over the lifetime of trees that are now in excess of 15 years of age indicates that the wood of scaffolds is resilient to bending under crops that have not been artificially thinned by either mechanical or human applied thinning means. The angle of initial scaffold limbs produced on 'Castleton' nursery trees grafted to 'Myrobolan Seedling' rootstocks average 68 degrees. Similar angles for 'Longjohn' cultivar average 60 degrees. Another important branching characteristic, besides relatively wide crotch angles, is that 'Castleton's' production of many lateral branches as compared to many other commercially important plum cultivars. 'Castleton' trees grafted to 'St Julian A' dwarfing rootstocks produce trees that are naturally dwarfed by approximately 40 percent. Hence they are well suited to home garden situations where space is often limited.

'Castleton' yields have usually been higher than 'Stanley' and always have surpassed that of the several strains of 'Italian Prune'. The improved yield potential over early ripening strains of 'Italian Prune' is one of the primary reasons for releasing the 'Castleton' cultivar, in that commercial orchardists in the Great Lakes Region have had a history of disappointing yields but they increasingly have been seeking a plum cultivar that will ripen before their 'Bartlett' pears and 'Gala' apples are ready for harvest. 'Castleton's' improved yield capability coupled with its fit to this fruit ripening "window" make it uniquely suited to this use. It usually surpasses strains of early 'Italian Prune' cultivar by over 100 percent in economic yield per acre in New York orchard trails.

Fruit losses due to natural dropping are quite low in the 'Castleton' cultivar when compared to the 'California Blue' and the 'Veeblue' varieties, which are known to be drop susceptible. 'Castleton' fruit drop is similar to 'Stanley'. Some economic losses can be expected with 'Castleton' due to changes in fruit quality if it is harvested after optimum harvest dates have been surpassed for the specific market use that is intended. However, it is the experience of the inventors that 'Castleton' fruit "hang well". This means that compared to other plums that ripe in the same general season, 'Castleton' fruit surpass them in capability to remain usable on the tree for longer periods of time. The early coloration of the skin of 'Castleton' is a unique feature that favors its early attainment of eye appeal for fresh market. Such early harvested fruit will have much lower sugar contents, but may have proven in pilot production and marketing trails to have adequate quality to have repeat sales to commercial buyers of fresh market plums. As is the case with all *Prunus domestica* kinds of plum cultivars flesh color gradually changes from green to different shades of greenish yellow to amber with the ripening process. 'Castleton' fruit flesh achieves a yellow-green 153D color at full tree-ripe and this color is hightly desirable for both fresh market and processed canned halves in light syrup as tested by pilot trails at the New York State Agricultural Experiment Station in the Department of Food Sciences and Technology by experienced food technologists.

DRIED PRUNE USAGE

No trails of the 'Castleton' prune for dried prune production and quality have been accomplished by the inventors or other researchers. Sugar content of the 'Castleton' fruit as grown in New York usually exceeds 20 percent, but commercial dried prune production is usually accomplished in more arid climates were summer night temperatures are much higher than in New York, and sugar contents are expected to be lower when nights are warmer. Hence, it is not possible to predict whether 'Castleton' fruit will be well suited to dried prune production in the primary commercial dried prune producing areas of the world. Similarly, hot climates often induce an objectionable physiological disorder which encourages the development of a waxy frass around the pit, call "pit burn" by professional prune plum breeders. It is not known by the inventors whether or not 'Castleton', when grown in a hot climate will be subject to pit burn. It has been noteworthy in its absence of this disorder in our New York trails. For home gardeners who grow 'Castleton' in the northern parts of the United States and other similar climates that are sufficiently favorable for trees fruits to live and fruit, home drying fruits in ovens can be expected to be highly successful in producing dried prunes because 'Castleton' in naturally sweet and has excellent flavor.

USEFULNESS

'Castleton' plum is well suited for production to fulfill certain commercial orchardist's needs for an early ripening season, high quality, dual purpose plum. The fruit color-up early making, it suited to mid-August harvest for commercial markets. They hold their quality exceptionally well both on the tree and in cold storage. The spreading, open habit of the 'Castleton' tree is well suited to either shake-and-catch mechanized harvesting for processing uses or for picking by hand. Numerous processing tests have proven 'Castleton' fruit produce high quality canned products that are comparable to or better than the commercial products made from other cultivars. A key feature that makes 'Castleton' highly likely to succeed as a processing plun cultivar is its pit shape that is conducive to easy mechanized removal and the pit's freeness from the flesh which also faclitates the mechanized pit removal task. The 'Stanley' cultivar, which was also invented at the New York State Agricultural Experiment Station, is prone to pitting faults during processing in some years. Home gardeners will appreciate this cultivar because of the same features that appeal to commercial producers.

What is claimed is:

1. A new and distinct plum tree as herein described and illustrated.

* * * * *